United States Patent [19]

Malabarba et al.

[11] Patent Number: 4,698,418

[45] Date of Patent: Oct. 6, 1987

[54] PROCESS FOR PREPARING ANTIBIOTIC L 17046

[75] Inventors: Adriano Malabarba; Bruno Cavalleri, both of Milan, Italy

[73] Assignee: Gruppo Lepetit, S.p.A., Gerenzano, Italy

[21] Appl. No.: 778,473

[22] Filed: Sep. 20, 1985

[51] Int. Cl.$^4$ .............................................. C07K 5/12
[52] U.S. Cl. .................................... 530/317; 530/332
[58] Field of Search ................................. 530/332, 317

[56] References Cited

U.S. PATENT DOCUMENTS

| 4,594,187 | 6/1986 | Strazzolini et al. | 530/332 |
| 4,629,781 | 12/1986 | Strazzolini et al. | 530/317 |
| 4,645,827 | 2/1987 | Malabarba et al. | 530/322 |

OTHER PUBLICATIONS

A. Malabarba, et al., J. Antibiotics 37(9), 988 (1984).
J. C. J. Barna, et al., J. Amer. Chem. Soc. 106(17), 4896, (1984).

*Primary Examiner*—Delbert R. Phillips
*Attorney, Agent, or Firm*—Stephen L. Nesbitt

[57] ABSTRACT

This invention relates to a process for converting a teicoplanin-like compound into antibiotic L 17046 characterized in that a teicoplanin-like compound selected from teicoplanin complex, any further purified preparation thereof, teicoplanin factor $A_2$, teicoplanin factor $A_3$, each of the main components of teicoplanin factor $A_2$, antibiotic L 17054 and a mixture of two or more of the above substances in any proportion is submitted to hydrolysis with a strong acid in the presence of a polar aprotic organic solvent selected from ethers, ketones and mixtures thereof that a room temperature are liquid.

7 Claims, No Drawings

PROCESS FOR PREPARING ANTIBIOTIC L 17046

The present invention is directed to a process for preparing a teicoplanin derivative named antibiotic L 17046. This antibiotic substance possesses antimicrobial activity mainly against gram-positive bacteria and is also a useful starting material to obtain deglucoteicoplanin.

In the copending European patent application No. 84102665.1 is described a partial hydrolysis of teicoplanin's factor $A_2$ yielding antibiotic L 17046. Said hydrolysis is carried out by treating teicoplanin factor $A_2$ with aqueous hydrochloric acid at a concentration from 1N to 3N at a temperature between 70° C. and 90° C. for 30 to 60 minutes.

Antibiotic L 17046 may be represented by the formula I below:

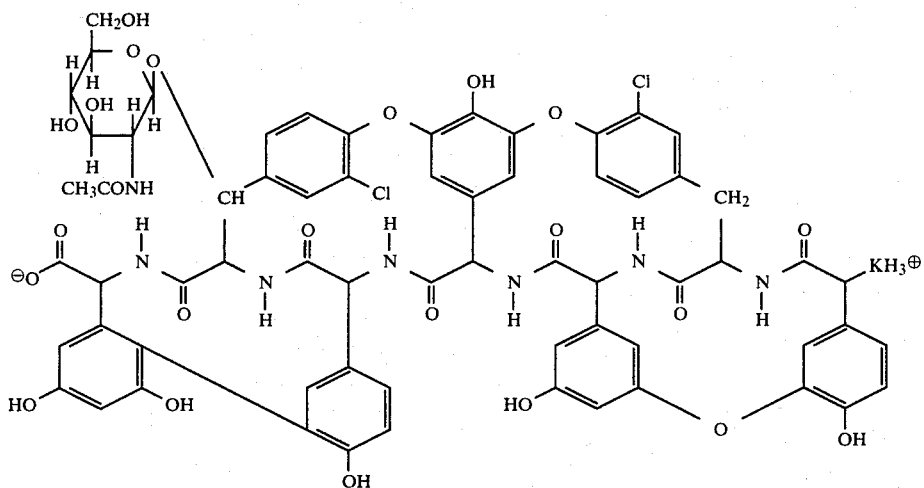

Teicoplanin is the international non-proprietary name (INN) of the antibiotic substance formerly named teichomycin which is obtained by cultivating the strain Actinoplanes teichomyceticus nov.sp. ATCC 31121 in a culture medium containing assimilable sources of carbon, nitrogen and inorganic salts (see U.S. Pat. No. 4,239,751). According to the procedure described in the above cited patent, an antibiotic complex (identified as teichomycin) containing factors $A_1$, $A_2$ and $A_3$ is recovered from the fermentation broth by extraction with a suitable water insoluble organic solvent and precipitation from the organic solvent according to common procedures. Factor $A_2$, which is the preponderant factor of the isolated antibiotic complex, is then separated from the other factors by means of column chromatography on Sephadex ®. Factor $A_1$ and factor $A_3$ are present only in minor amounts.

British patent application Publication No. 2121401 discloses that antibiotic factor $A_2$, in turn, actually is a mixture of five closely related co-produced main components.

From fermentation and purification (for instance, through column chromatography) operations a teicoplanin product is currently obtained which essentially consists of factor $A_2$ accompanied by minor amounts of factor $A_3$.

Recent studies shows that teicoplanin factor $A_2$ and its individual main components may be represented by a general formula II of this type

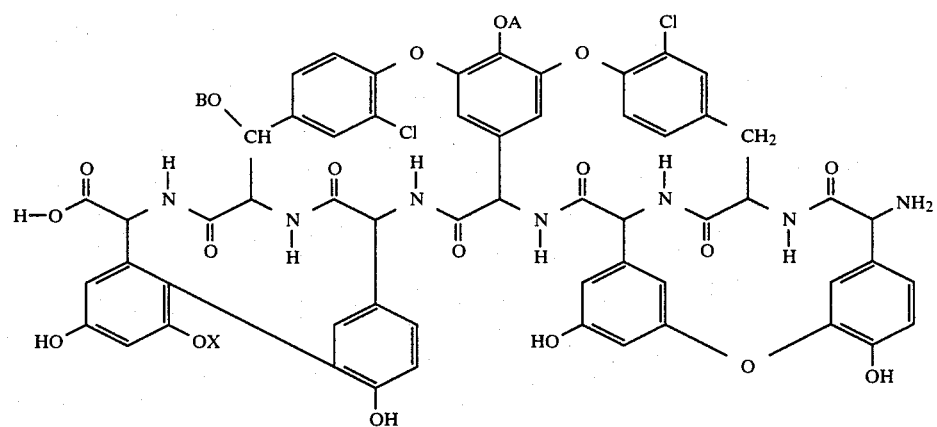

wherein

A is a N-[($C_{10}$-$C_{11}$)aliphatic acyl]-D-glucosamine group,

B is a N-acetyl-D-glucosamine group, and

X is a D-mannose group.

All sugar moieties identified above are linked to the basic molecule through O-glycosidic bonds. In the copending European patent application No. 84102666.9 is described a partial hydrolysis products of teicoplanin's factor $A_2$ wherein one sugar moiety is split off. This product is named antibiotic L 17054. This product is obtained by submitting teicoplanin factor $A_2$ to specific acid hydrolysis conditions, preferably, by using 0.5N hydrochloric acid at a temperature between 70° C. and 90° C. for 15 to 90 minutes. Antibiotic L 17054 may be represented by the formula II above, wherein A is replaced by hydrogen, B is a N-acetyl-D-glucosamine group and X is a D-mannose group.

In this specification and claims, with the term "teicoplanin compound" it is indicated a substance selected from teicoplanin complex obtained by fermentation of *Actinoplanes teichomyceticus* ATCC 31121 followed by purification operations according to U.S. Pat. No. 4,239,751, any further purified preparation thereof, teicoplanin factor $A_2$, teicoplanin factor $A_3$, each of the main components of teicoplanin factor $A_2$, antibiotic L 17054, and a mixture of two or more of any of the above substances in any proportion.

The object of this invention is to provide a new and more efficient process for obtaining antibiotic L 17046 by acid hydrolysis of a teicoplanin compound. More particularly, it has been found that antibiotic L 17046 may be obtained in high yields from a teicoplanin compound by hydrolysis with a strong acid in the presence of polar aprotic organic solvent selected from ethers, ketones and mixtures thereof that at room temperature are liquids.

In summary, the object of this invention is a process for converting a teicoplanin-like compound into antibiotic L 17046 characterized in that a teicoplanin-like compound selected from teicoplanin complex, any further purified preparation thereof, teicoplanin factor $A_2$, teicoplanin factor $A_3$, each of the main components of teicoplanin factor $A_2$, antibiotic L 17054 and a mixture of two or more of the above substances in any proportion is submitted to hydrolysis with a strong acid in the presence of a polar aprotic organic solvent selected from ethers, ketones and mixtures thereof that a room temperature are liquid. The term "ethers" includes cyclic ethers and di-ethers. According to a preferred embodiment of this invention the term "ethers" is identified through the following general formulas III and IV

$$R-O-R_1 \text{ and } R_2O-(CH_2)_n-OR_3$$

III        IV where R and $R_1$ may be each independently selected from alkyl of 1 to 8 carbon atoms, cycloalkyl of 5 to 8 carbon atoms, phenyl and phenyl-$(C_1-C_4)$alkyl or taken together with the oxygen atom form a fully hydrogenated heterocyclic ring of 5 to 10 members; n is the integer 2 or 3 and $R_2$ and $R_3$ are each independently selected from lower alkyl of 1 to 4 carbon atoms, phenyl and phenyl-$(C_1-C_4)$alkyl or taken together with the group —O—$(CH_2)_n$—O— form a fully hydrogenated 5 to 10 heterocyclic ring. Specific examples of said ethers are the following: diethyl ether, methyl propyl ether, methyl butyl ether, dipropyl ether, dibutyl ether, methyl diisopropyl ether, benzyl methyl ether, benzyl ethyl ether, ethyl isobutyl ether, ethyl isopropyl ether, ethyl diisobutyl ether, ethyl pentyl ether, dioctyl ether, ethyl octyl ether, ethyl cyclohexyl ether, methyl benzyl ether, methyl (2-phenyl)ethyl ether, dibenzyl ether, propyl cyclohexyl ether, ethoxy benzene, methoxy benzene, tetrahydrofuran, tetrahydropyran, 2,5-dimetyltetrahydropyran, 1,2-dimethoxyethane, 1,2-diethoxyethane, 1,2-diisobutoxyethane, 1-ethoxy-2-methoxyethane, 1,2-dimethoxypropane, 1,2-diethoxypropane, 1,3-dimethoxypropane, 1,3-diethoxypropane, 1,2-dibutoxyethane, 1-benzyloxy-2-methoxyethane, 1,4-dioxane. The term "ketones" refers to aliphatic ketones of 3 to 8 carbon atoms and includes cycloaliphatic ketones of 5 to 8 carbon atoms. According to a preferred embodiment of this invention the "ketones" are identified by the following formula V

$$R_4-CO-R_5 \qquad V$$

wherein $R_4$ and $R_5$ are each independently selected from lower alkyl of 1 to 6 carbon atoms with the proviso that the total number of carbon atoms in the above formula V can never be higher than 8 or $R_4$ and $R_5$ taken together form a polymethylene chain of 4 to 7 carbon atoms. Examples of said ketones are the following: acetone, 2-butanone, 2-pentanone, 3-pentanone, 2-hexanone, 3-hexanone, 2-heptanone, 3-heptanone, 4-heptanone, 2-octanone, 3-octanone, 4-octanone, cyclopentanone, cyclohexanone, cycloheptanone, cyclooctanone. Although in the description and claims the term "solvent" is employed, according to the process of this invention it is not necessary that either the starting teicoplanin compound and/or the final antibiotic L 17046 product is completely dissolved into the reaction solvent to form a homogeneous phase reaction solution. It is however necessary that the starting teicoplanin compound at the reaction temperature is dissolved into the polar aprotic organic solvent/strong acid mixture in a sufficient amount, that is, the concentration of the starting teicoplanin compound in the solution must not be so low that the reaction rate is very slow and/or a huge amount of solvents is required to perform the reaction in a pilot or industrial scale. Among the solvents listed above the following are particularly preferred for the use in the acid hydrolysis reaction: tetrahydrofuran, tetrahydropyran, 1,2-dimethoxyethane, 1,2-diethoxyethane, dioxane and mixtures thereof. The solvent is usually employed in a large excess in comparison with the starting teicoplanin compound. Although the most suitable amount of solvent can be determined in each case depending on the specific type of solvent, in particular on its solvent power and its boiling point, and on the type of acid employed, in general it is preferred to carry out the acid hydrolysis in the presence of an amount of polar aprotic organic solvent corresponding to 10 to 50 milliliters of solvent per each gram of starting teicoplanin compound.

The strong acid necessary to carry out the hydrolysis reaction is selected from strong mineral acids and strong organic acids. Among the strong mineral acids hydrogen chloride, hydrogen bromide, concentrated sulfuric acid and concentrated phosphoric acid are preferred. Among the strong organic acids the alphahalogenated lower aliphatic acids, the alkanesulfonic acids, the polyfluoroalkanesulfonic acids, the cycloalkanesulfonic acids and the arylsulfonic acids are preferred with the following being the most preferred ones: trifluoroacetic acid, trichloroacetic acid, methanesulfonic acid, ethanesulfonic acid, trifluoromethanesulfonic acid and p-toluenesulfonic acid. The concentrated acids are preferably employed in large weight excess on the starting teicoplanin compound. When the acid is a gas soluble in the polar aprotic organic solvent (e.g. HCl and HBr) this latter is saturated by bubbling the acid gas into the reaction mixture and saturation is maintained during at least the initial period of the reaction by continuously bubbling the acid gas. Sulfuric acid and phosphoric acid are usually employed at the highest concentration commercially available. In particular, 95% to 98% (w/w) sulfuric acid and 85% to 98% (w/w) orthophosforic acid, yield satisfactory results. Among the organic acids, 98% (w/w) methanesulfonic acid and 98% (w/w) trifluoroacetic acid are preferably employed according to one embodiment of this invention.

The content of water in the reaction mixture must be sufficient to meet the stoichiometric requirement of the hydrolysis reaction. On the other side, it is desirable to keep the amount of water in the reaction mixture as lower as possible to prevent unwanted side reactions such as further hydrolysis or degradation of the reaction product, or rearrangement and/or isomerization of the chiral centers of the substrate. For meeting the stoichiometric requirements of the reaction and, at the same time, keeping the rate and the process operability at an industrially valuable level, the hydrolysis process is usually carried out in the presence of an amount of water which ranges from about 3% to about 100% by weight, preferably from about 5% to about 50% by weight of the starting teicoplanin compound.

The sufficient water amount may be supplied together with the acid or it may be originally contained in the starting teicoplanin compound. When essentially anhydrous starting material, solvent and acid are employed, the desired amount of water may be directly added to the solvent or to the reaction mixture. The temperature of the process essentially depends on the type of acid and solvent employed. In general, temperatures between 0° and 60° C. are suitable with the range between 10° C. and 40° C. being preferred.

The reaction time may suitably be determined by following the reaction course through analytical tests, for example, the High Performance Liquid Chromatography (HPLC). When the analytical tests show a satisfactory conversion yield of the starting teicoplanin compound into the desired antibiotic L 17046, the reaction is stopped and the recovery of the reaction product is carried out in the usual way.

In frequent cases the reaction mixture during all reaction time is a suspension of both starting material and end product in the selected polar aprotic organic solvent (e.g. in most cases where the solvent is tetrahydrofuran and the acid is HCl or HBr gas). In other cases the starting reaction mixture is a suspension and the final reaction mixture is a solution. (e.g. when the acid is concentrated sulfuric acid and the solvent is tetrahydrofuran or acetone). Although the reaction time may be typical of each reaction system and the relative operational temperature, in general the reaction is completed within 2 to 60 hours. In particular, when the acid gas is bubbled into the reaction vassel maintaining acid saturation conditions, bubbling is generally continued at the selected reaction temperature, with stirring, for 2 to 6 hours since the beginning of the reaction, then it is suspended and the reaction mixture is stirred for additional 5 to 20 hours at a temperature between 20° C. to 30° C.

When the reaction is complete, the recovery of the end product is carried out in the usual way. If a substantial amount of end product is contained in the final reaction mixture as a solid precipitate, it is separated by filtration or centrifugation. The remaining organic solvent is discarded or, if HPLC tests show that it contains additional amount of the end product, it is set apart for the recovery of said product. When most of the end product is dissolved in the polar aprotic organic solvent it may be precipitated by addition of a further solvent where it is substantially insoluble, e.g. diethyl ether. The product directly recovered from the reaction mixture is in general in the form of an acid addition salt with the same strong acid employed in the hydrolysis reaction. Said product is usually further purified and transformed into the acid free compound by common procedures. These procedures include dissolution of the product into water containing from 10% to 50% by volume of a water soluble lower alkanol (e.g. methanol or ethanol), followed by extraction of the aqueous layer with organic solvents or their mixture which are slightly soluble into water (e.g. mixture of n-butanol and lower alkyl acetates or lower alkyl ethers).

The aqueous layer containing the end product as a salt with the strong acid is then adjusted to pH 5.9 to precipitate the acid free product, which is recovered and dried under reduced pressure to yield substantially pure antibiotic L 17046.

Antibiotic L 17046 which has been disclosed in European patent application No. 84102665 has the following characteristics:

(a) the specific rotation $[\alpha]_D^{20}$ is $-44°$ (c=1%, DMF)

(b) it is freely soluble in water at pH>8.0, in dimethylformamide, dimethylsulfoxide, propyleneglycol and methylcellosolve; slightly soluble in methanol; almost insoluble in n-hexane, diethyl ether and acetone.

(c) it has an ultraviolet absorption spectrum, that exhibits the following absorption maxima:
in 0.1N hydrochloric acid: $\lambda_{max}$ 278 nm ($E_{1cm}^{1\%}=67.1$)
in 0.1N sodium hydroxide: $\lambda_{max}$ 297 nm ($E_{1cm}^{1\%}=124.1$)
in phosphate buffer pH 7.4: $\lambda_{max}$ 277 nm ($E_{1cm}^{1\%}=75.0$)

(d) an infrared absorption spectrum in nujol with the following observable absorption maxima (cm$^{-1}$): 3700-2000, 2970-2850 (nujol), 1655, 1610, 1595, 1515, 1490, 1460 (nujol), 1375 (nujol), 1300, 1230, 1145, 1060, 1010, 890, 850, 820, 720 (nujol)

(e) an elemental analysis, after the sample has been previously dried at about 140° C. under inert atmosphere (weight loss=8.4%), which indicates the following approximate percentage composition (average): carbon 56.74%; hydrogen, 4.27%; nitrogen, 7.99%; chlorine, 5.11%; ashes, 0.6%

(f) the following R$_f$ values in the TLC systems indicated below:

| | Elution system (v/v) | R$_f$ value |
|---|---|---|
| I | Acetonitrile/water 75:25 (silica gel Merck 60 F$_{254}$) | 0.53 |
| II | Acetonitrile/5% aqueous sodium sulfate 30:70 (silica gel Merck silanized 60 F$_{254}$) Visualization: UV-light at 254 nm; 3% ethanolic ninhydrine; 1% methanolic fluorescamine; | 0.54 |

(g) a retention time (t$_R$) of 10.8 minutes when analyzed by reversed phase HPLC using a 150×4.0 mm Zorbax ® ODS (5-6 um) column (Zorbax is a trademark of the Dupont Co. for a octadecylsilane silica matrix), and eluting with a linear gradient from 0% to 50% solution B in solution A in 40 minutes solution A: 25 mM $NaH_2PO_4$/acetonitrile (9/1) buffered at pH 6.0 with 0.1N NaOH solution B: 25 mM $NaH_2PO_4$/acetonitrile (3/7) buffered at pH 6.0 with 0.1N NaOH), with a flow rate of 2 ml/min; (internal standard: 3,5-dihydroxytoluene $t_R$ 5.60 minutes)

(h) the $^1H$ NMR spectrum registered at 270 MHz in DMSO-$d_6$ at 60° C. and with a sample concentration of 20 mg/ml (internal standard, TMS $\delta=0.00$ ppm). Some of the $^1H$ NMR data obtained after $D_2O$ exchange and selective decoupling experiments are as follows ($\delta$ ppm, multiplicity): 1.86, s; 2.81, d; 3.5, dd; 3-4; 4.12, d; 4.32, d; 4.37, d; 4.56, s; 4.95, ddd; 5.07, s; 5.31, d; 5.39, s; 5.51, s; 5.66, d; 6.12, d; 6.29, s; 6.32, s; 6.37, s; 6.42, s; 6.60, d; 6.62, s; 6.64, d; 6.92, d; 7.09, s; 7.12, d; 7.21, d; 7.25, d; 7.43, d; 7.64, d; 7.66, d; 7.70, d; 7.85, s; 8.12, d; 8.46, d; 9.5, s.

(i) a potentiometric titration profile which shows titration slopes with pH ½ values equal to 5.0 (one equivalent), 7.0 (one equivalent), upon titration with 0.01N NaOH of a solution of the test compound containing an excess of 0.01N HCl in the same solvent mixture, and a titration slope with pH ½ value of 12.8 (five equivalents) upon titration with 0.1N KOH of a solution of the test compound in dimethylformamide/water, 9:1 containing an excess of 0.1N HCl in the same solvent mixture.

(l) an acidic function capable of forming salts (m) a basic function capable of forming salt (n) a sugar residue which is N-acetyl-D-glucosamine.

On the basis of the physico-chemical data and by comparison with other glycopeptidic antibiotic substances, such as vancomycin and ristocetin, the following structure can tentatively be attributed to antibiotic L 17046:

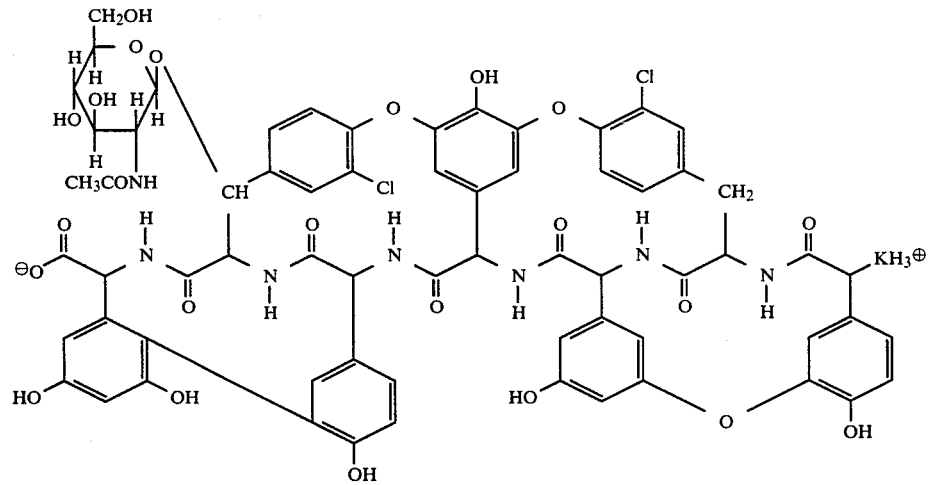

If the crude product directly obtained from the reaction mixture contains a certain amount of impurities deriving from further hydrolysis or degradation which cannot be eliminated with the procedure described above, column chromatography purification may be applied. According to a preferred method of chromatographic purification the crude product is dissolved in a water:acetonitrile 9:1 (v/v) mixture adjusted to pH 1.9 by addition of aqueous mineral acid and then chromatographed through a silanized silica-gel column stabilized with 1% aqueous ammonium formate. If necessary, the pH of the eluted fractions is adjusted to 5.9 by additions of aqueous mineral acid or base.

The following examples further illustrate the invention and are not to be construed as limiting its scope.

EXAMPLE 1

40 g of teicoplanin complex (e.g. the antibiotic complex containing teicomycin factors $A_1$, $A_2$ and $A_3$ obtained by fermentation of strain ATCC 31121 according to U.S. Pat. No. 4,239,751) containing 10% by weight of water (Karl Fischer method) are suspended into 800 ml of dry tetrahydrofuran saturated with dry HCl. The reaction mixture is stirred at 25° C.–30° C. while bubbling gaseous HCl for 3 hours. Then, bubbling of HCl is suspended and the mixture is stirred for additional 12 hours at 25° C. The insoluble material is collected on filter, washed with 500 ml of diethyl ether and then with 100 ml of acetone. The solid is dried overnight under vacuum (0.5 mmHg) yielding 30.4 g of a crude product which is dissolved in 2 liters of a mixture water: methanol 4:1 (v/v). Then a mixture of 3 liters of water, 2 liters of ethyl acetate and 2 liters of n-butanol is added thereto with vigorous stirring. After staying overnight, the aqueous layer is separated and then concentrated under vacuum (15 mmHg) at 45° C. to a final volume of 400 ml. By adjusting the pH to 5.9 with 1N NaOH a solid precipitate is obtained. The solid is collected on filter, washed with 400 ml of water, and successively with 400 ml of diethyl ether and 200 ml of acetone. After drying the solid for 24 hours under vacuum (0.5 mmHg) at 45° C., 24.5 g of essentially pure antibiotic L 17046 is obtained (HPLC title higher than 95%; water content usually lower than 10% by weight). The product has the physico-chemical characteristics described above.

EXAMPLE 2

2.35 g of teicoplanin factor $A_2$ (e.g. teicomycin $A_2$ as obtained according to U.S. Pat. No. 4,239,751) containing 10% of water by weight are treated in the same manner as described in Example 1 above by using the appropriate proportions of solvents and reagents. The yield of substantially pure antibiotic L 17046 is 1.62 g.

EXAMPLE 3

(a) preparation of antibiotic L 17054

Five grams of teicoplanin complex containing 10% of water is added to 60 ml of 0.5N aqueous hydrochloric acid pre-heated to 80° C. with vigorous stirring.

Stirring is continued and the temperature is maintained at about 80° C. for 30 minutes. Then, the mixture is rapidly filtered, the filtrate is cooled to 0-5° C. and 6N hydrochloric acid (10 ml) is added. The resulting suspension is stirred for about 15 minutes while keeping the temperature at 0°-5° C. The precipitate is collected, washed with 20 ml of cold 1N HCl and then with diethyl ether, and dried under reduced pressure at room temperature resulting in crude antibiotic L 17054 hydrochloride (4.5 g).

A sample of this product may be purified according to the following procedure:

Crude antibiotic L 17054 hydrochloride (3 g) is suspended in a mixture of 0.2% aqueous ammonium formate/acetonitrile 95:5 (v/v) (150 ml).

The pH is brought to about pH 7.5 with 1N NaOH and the product is dissolved. The resulting solution is applied to a column containing 150 g of silanized silica gel (0.06-0.2 mm, Merck) prepared in the same solvent mixture. The column is developed with a linear gradient elution, from 5 to 21% of acetonitrile in 0.2% aqueous ammonium formate (v/v), collecting 20 ml fractions, which are monitored by HPLC. L 17054 containing fractions (70 to 96) are combined and the acetonitrile is removed under vacuum. The residual aqueous solution is applied to a column of 10 g of silanized silica gel (0.06-0.2 mm, Merck) in distilled water. After washing with distilled water until the salts are completely eliminated, the product is eluted with a mixture acetonitrile/water 1:1 (v/v).

The collected solution is concentrated under vacuum to a small volume and the antibiotic is precipitated by adding acetone.

After drying at room temperature, 0.9 g of pure antibiotic L 17054 is obtained.

L 17054 has the following characteristics:

(a) the specific rotation $[\alpha]_D^{20}$ is $-34°$ (c=1%, DMF)

(b) it is freely soluble in water at pH>8.0, in dimethylformamide, dimethylsulfoxide, propyleneglycol and methylcellosolve; slightly soluble in methanol; almost insoluble in diethyl ether and acetone.

(c) an ultraviolet absorption spectrum which has the following absorption maxima:

in 0.1N hydrochloric acid: $\lambda_{max}$ 278 nm ($E_{1cm}^{1\%}=60.6$)

in 0.1N sodium hydroxide: $\lambda_{max}$ 297 nm ($E_{1cm}^{1\%}=118.8$)

in phosphate buffer pH 7.4: $\lambda_{max}$ 277 nm ($E_{1cm}^{1\%}=70.3$)

(d) an infrared absorption spectrum in nujol with the following absorption maxima (cm$^{-1}$): 3700-2000, 2970-2850 (nujol), 1655, 1610, 1595, 1515, 1490, 1460 (nujol), 1375 (nujol), 1300, 1230, 1145, 1060, 1020, 970, 890, 850, 820, 720 (nujol)

(e) an elemental analysis, after the sample has been previously dried at about 140° C. under inert atmosphere (weight loss=7.8%), which indicated the following approximate percentage composition (average): carbon 55.46%; hydrogen, 4.50%; nitrogen 7.20%; chlorine 4.67%; ashes 0.2%

(f) it has the following $R_f$ values in the TLC systems indicated below:

| | Elution system (v/v) | $R_f$ value |
|---|---|---|
| I | Acetonitrile/water 75:25 (silica gel Merck 60 F$_{254}$) | 0.32 |
| II | Acetonitrile/5% aqueous sodium sulfate 30:70 (silica gel Merck silanized 60 F$_{254}$) Visualization: UV-light at 254 nm; 3% ethanolic ninhydrine; 1% methanolic fluorescamine; | 0.61 |

(g) a retention time ($t_R$) of 8.3 minutes when analyzed by HPLC using a 150×4.0 mm Zorbax® ODS (5-6 μm) column (Zorbax is a trademark of the Dupont Co. for an octadecylsilane silica gel matrix), and eluting with a linear gradient from 0% to 50% solution B in solution A in 40 minutes (solution A: 25 mM NaH$_2$PO$_4$/acetonitrile 9:1, buffered at pH 6.0 with 0.1N NaOH; solution B: 25 mM NaH$_2$PO$_4$/acetonitrile 3:7, buffered at pH 6.0 with 0.1N NaOH), with a flow rate of 2 ml/min.; (internal standard: 3,5-dihydroxytoluene $t_R$ 5.60 minutes)

(h) the $^1$H NMR spectrum is registered at 270 MHz in DMSO-d$_6$ at 60° C. and with a sample concentration of 20 mg/ml (internal standard TMS, $\delta=0.00$ ppm). Some of the $^1$H NMR data obtained after D$_2$O exchange and selective decoupling experiments are as follows $\delta$ ppm, multiplicity): 1.88, s; 2.85, d; 3.5, dd; 3-4; 4.20, d; 4.48, d; 4.50, d; 4.62, s; 4.96, ddd; 5.18 d; 5.31, s; 5.35, d; 5.39, s; 5.68, d; 5.71, s; 6.20, d; 6.41, s; 6.51, s; 6.56, s; 6.74, d; 6.77, s; 6.80, s; 6.80, d; 6.98, d; 7.08, s; 7.15, d; 7.21, d; 7.28, d; 7.35, d; 7.50, d; 7.56, d; 7.64, d; 7.73, d; 7.86, s; 8.42, d.

(i) a potentiometric titration profile which shows two titration slopes with pH ½ values equal to 5.0 (one equivalent), 7.0 (one equivalent in methylcellosolve/water 4:1 upon tritating a solution of the test compound containing an excess of 0.01N HCl in methylcellosolve/water 4:1 with 0.01N NaOH in the same solvent mixture, and a tritation slope with pH ½ value 12.8 (five equivalents) upon titration with 0.1N KOH of solution of the test compound in DMF/water 9:1 containing an excess of 0.1N HCl in the same solvent mixture.

(l) an acidic function capable of forming salts (m) a basic function capable of forming salts (n) two sugar residues which are D-mannose and N-acetyl-D-glucosamine.

On the basis of the physico-chemical data and by comparison with the structures known for other glycopeptidic antibiotic substances, such as vancomycin and ristocetin, the following structure can be attributed to antibiotic L 17054:

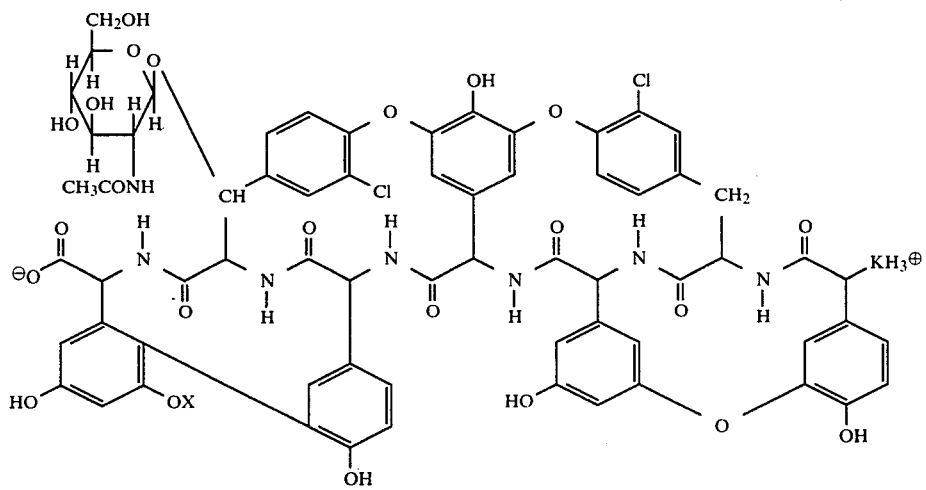

wherein X is an α-D-mannose group.

(b) preparation of antibiotic L 17046.

3.7 g of crude antibiotic L 17054 hydrochloride containing 11% by weight of water is suspended in 80 ml of dry tetrahydrofuran saturated with dry HCl. The reaction mixture is stirred for 2 hours at 25° C.-30° C. while bubbling dry HCl. Then, bubbling of HCl is suspended and the reaction mixture is allowed to stand for six hours with stirring at 25° C. The insoluble material is then collected on filter, washed successively with 200 ml of diethyl ether and with 100 ml of acetone. The solid is then dried overnight and purified following the same procedure described in the last part of Example 1 by using the appropriate proportions of solvents and reagents. Yield 2.98 g of essentially pure antibiotic L 17046.

EXAMPLE 4

11 g of teicoplanin complex containing 20% by weight of water is treated according to the procedure of Example 1 yielding 8.3 g of crude product. This crude product which contains also about 17% (HPLC analysis) of undesired side products deriving from further hydrolysis of antibiotic L 17046 is purified according to the following procedure. It is dissolved in 1 liter of a mixture water/methanol 4:1 (v/v) and 1N HCl is added thereto to pH 1.8. Then, 2.4 liters of a mixture of n-butanol/water 1:1 (v/v) is added to the above solution with vigorous stirring. After standing one night at room temperature, the aqueous layer is separated and concentrated under vacuum (15 mmHg) at 45° C. to a volume of 250 ml. The pH of the mixture is adjusted to 5.9 by addition of 1N NaOH and the solid which separates is collected on filter, washed with 100 ml of water and, successively, 200 ml of diethyl ether and 100 ml of acetone. The product is dried overnight under vacuum (0.5 mmHg) at 45° C. yielding 3.48 g of essentially pure antibiotic L 17046.

The above organic layer is worked out according to the following procedure to recover some additional end product. The organic layer is concentrated to a small volume under vacuum (15 mmHg), then 500 ml of diethyl ether are added thereto. The solid precipitate is collected on filter, washed with 100 ml of diethyl ether and dried under vacuum (0.5 mmHg) at room temperature overnight yielding 2.71 g of crude product. This crude product is suspended in 200 ml of a mixture water/acetonitrile 9:1 (v/v) and the pH of the mixture is adjusted to 1.9 by adding 1N HCl. The resulting solution, after addition of 200 ml of water, is loaded on a column of 300 g of silanized silica-gel (0.06–0.20 mm, Merck) stabilized with 1% aqueous ammonium formate at a rate of 200 ml/hours. Fractions of 20 ml each are collected and monitored by HPLC. The fractions containing essentially pure L 17046 are combined and concentrated under vacuum (15 mmHg) at 40° C. to a small volume (if necessary the pH is adjusted to 5.9 by addition of 1N NaOH or 1N HCl). The solid precipitate is collected on filter, washed with water and then with diethyl ether. After drying under vacuum (0.5 mmHg) overnight, additional 1.37 g of essentially pure antibiotic L 17046 are obtained.

EXAMPLE 5

To a solution of 40 ml of 96% (w/w) sulfuric acid in 80 ml of tetrahydrofuran, 4.5 g of teicoplanin complex containing 10% by weight of water are added with stirring at 3° C. The reaction mixture is then stirred at 15° C.-20° C. for two days while a dark brown solution is obtained. By addition of 1 liter of diethyl ether a sticky solid forms which is separated and then triturated with 100 ml of a mixture of diethyl ether/methanol 4:1. The powder obtained is collected on filter, washed with 100 ml of diethyl ether and dried under vacuum (0.5 mmHg) at 50° C. overnight yielding 3.8 g of a crude product which is purified as described in Example 4. After this purification procedure two crops respectively of 1.25 and 0.53 g (column chromatography) of essentially pure antibiotic L 17046 are obtained.

EXAMPLE 6

4.5 g of teicoplanin complex containing 10% by weight of water is suspended in 150 ml of acetone and 10 ml of 96% (w/w) sulfuric acid are added dropwise with stirring at 15° C.-20° C. A clear solution forms after about 30 minutes. The mixture is stirred at room temperature overnight, then 800 ml of diethyl ether are added and the solid precipitate is collected on filter, washed with diethyl ether and dried under vacuum (0.5 mmHg) at room temperature to yield 3.68 g of crude product. This crude product is purified by chromatography on silanized silica-gel column as described in the last part of Example 4.

Yield 1.18 g of essentially pure antibiotic L 17046.

EXAMPLE 7

8.5 g of teicoplanin factor $A_2$ containing 10% by weight of water are suspended into 200 ml of 1,2-dimethoxyethane saturated with dry HCl. The reaction mixture is stirred at 25° C.-30° C. while bubbling dry HCl for 2.5 hours. Bubbling of HCl is suspended and the mixture is allowed to stand for 12 hours at 25° C. Then 600 ml of diethyl ether are added and the solid precipitate is collected on filter, washed with 200 ml of diethyl ether and then with 100 ml of acetone. After drying overnight the solid is purified according to the procedure described in Example 1.

Yield 5.5 g of essentially pure antibiotic L 17046.

EXAMPLE 8

2.5 g of a mixture of teicoplanin factor $A_2$ and teicoplanin factor $A_3$ (factor $A_2$: 80% by weight; factor $A_3$: 9.5% by weight; water : 10.0% by weight; inorganic salts: 0.5% by weight) are treated in the same manner as described in Example 1 by using HBr gas instead of HCl gas and employing the appropriate proportions of solvent and reagents.

Yield 1.6 g of substantially pure antibiotic L 17046.

EXAMPLE 9

4.5 g of teicoplanin complex containing 10% by weight of water are treated in the same manner as described in Example 5 by using dry methanesulfonic acid instead of sulfuric acid and employing the appropriate proportions of solvents and reagents.

Yield 0.9 and 0.7 g (column chromatography) of essentially pure antibiotic L 17046.

We claim:

1. A process for converting a teicoplanin compound into antibiotic L 17046 characterized in that a teicoplanin compound selected from teicoplanin complex, any further purified preparation thereof, teicoplanin factor $A_2$, teicoplanin factor $A_3$, each of the main components of teicoplanin factor $A_2$, antibiotic L 17054 or a mixture of two or more of the above substances in any proportion is submitted to hydrolysis with a strong acid in the presence of a polar aprotic organic solvent selected from ethers, ketones, and mixtures thereof, which are liquid at room temperature.

2. A process according to claim 1 wherein the polar aprotic organic solvent is selected from ethers and ketones respectively of formula III, IV and V

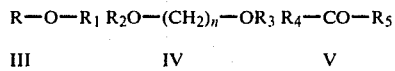

wherein R and $R_1$ are each independently selected from alkyl of 1 to 8 carbon atoms, cycloalkyl of 5 to 8 carbon atoms, phenyl and phenyl-$(C_1-C_4)$alkyl or R, and $R_1$ taken together with the oxygen atom form a fully hydrogenated heterocyclic ring of 5 to 10 members; n is the integer 2 or 3 and $R_2$ and $R_3$ are each independently selected from alkyl of 1 to 4 carbon atoms, phenyl and phenyl-$(C_1-C_4)$alkyl or $R_2$ and $R_3$ taken together with the group $-O-(CH_2)_n-O-$ form a fully hydrogenated 5 to 10 membered heterocyclic ring; $R_4$ and $R_5$ are each independently selected from lower alkyl of 1 to 6 carbon atoms, with the proviso that the total number of carbon atoms in the above compounds of formula V can never be higher than 8, or $R_4$ and $R_5$ taken together form a polymethylene chain of 4 to 7 carbon atoms; and the strong acid is selected from strong mineral acids and strong organic acids.

3. A process according to claims 1 and 2 wherein the strong acid is selected from hydrogen chloride, hydrogen bromide, sulfuric acid, phosphoric acid, trifluoroacetic acid, trichloroacetic acid, methanesulfonic acid, ethanesulfonic acid, trifluoromethanesulfonic acid and p-toluenesulfonic acid.

4. A process according to claim 3 wherein the strong acid is selected from hydrogen chloride, hydrogen bromide, concentrated sulfuric acid, concentrated orthophosphoric acid, concentrated methanesulfonic acid and concentrated trifluoroacetic abid.

5. A process according to claim 1, 2, 3 or 4 wherein the acid hydrolysis is carried out in the presence of an amount of polar aprotic organic solvent corresponding to 10 to 50 milliliter of said solvent per each gram of starting teicoplanin compound.

6. A process according to claim 1, 2, 3, 4 or 5 when carried out in the presence of an amount of water ranging from about 5% to about 50% by weight of the starting teicoplanin compound.

7. A process according to claim 1, 2, 3, 4, 5 or 6 wherein the reaction temperature range is between 10° C. and 40° C.

* * * * *